United States Patent
Cyganek (10) Patent No.: US 12,312,630 B2
(45) Date of Patent: May 27, 2025

(54) DEVICE AND METHOD FOR THE MICROBIOLOGICAL EXAMINATION OF WASHING MACHINES

(71) Applicant: Meducomp GmbH, Herzfelde (DE)

(72) Inventor: Jürgen Cyganek, Herzfelde (DE)

(73) Assignee: Meducomp GmbH, Herzfelde (DE)

( * ) Notice: Subject to any disclaimer, the term of this patent is extended or adjusted under 35 U.S.C. 154(b) by 553 days.

(21) Appl. No.: 16/650,902

(22) PCT Filed: Oct. 1, 2018

(86) PCT No.: PCT/EP2018/076642
§ 371 (c)(1),
(2) Date: Mar. 26, 2020

(87) PCT Pub. No.: WO2019/063840
PCT Pub. Date: Apr. 4, 2019

(65) Prior Publication Data
US 2020/0232006 A1    Jul. 23, 2020

(30) Foreign Application Priority Data

Sep. 29, 2017 (DE) .......................... 202017105965.0
Sep. 29, 2017 (EP) ..................................... 17193973

(51) Int. Cl.
*C12Q 1/04* (2006.01)
*A61L 2/28* (2006.01)
(Continued)

(52) U.S. Cl.
CPC ............... *C12Q 1/04* (2013.01); *B01L 3/508* (2013.01); *A61L 2/28* (2013.01);
(Continued)

(58) Field of Classification Search
CPC ... C12Q 1/22; C12Q 1/04; C12Q 1/18; C12Q 1/02; B01L 2300/123; B01L 2300/165;
(Continued)

(56) References Cited

U.S. PATENT DOCUMENTS 3,346,464 A   10/1967   Ernst
4,743,537 A   5/1988    McCormick et al.
(Continued)

FOREIGN PATENT DOCUMENTS

DE    37 05 596 A1    9/1988
GB    1 055 387 A     1/1967
(Continued)

OTHER PUBLICATIONS

International Search Report and Written Opinion for International Application No. PCT/EP2018/076642, mailed Oct. 29, 2018.
(Continued)

*Primary Examiner* — Kathryn Elizabeth Limbaugh
(74) *Attorney, Agent, or Firm* — Wolf, Greenfield & Sacks, P.C.

(57) ABSTRACT

The invention relates to a bioindicator and a method for using the bioindicator for microbiological testing of washing machines. The device according to the invention allows a safe, reliable, cost-effective and easy-to-use microbiological test of the disinfection performance of washing machines. The invention further relates to a use of the bioindicator and a kit comprising 10 bioindicators. In particular, the invention relates to a closed bioindicator for a verification of disinfecting washing processes.

18 Claims, 2 Drawing Sheets

(51) Int. Cl.
  *B01L 3/00* (2006.01)
  *C12M 1/12* (2006.01)
  *C12Q 1/02* (2006.01)
  *C12Q 1/18* (2006.01)
(52) U.S. Cl.
  CPC ............... *B01D 2325/02834* (2022.08); *B01L 2300/123* (2013.01); *B01L 2300/165* (2013.01); *C12M 37/06* (2013.01); *C12Q 1/02* (2013.01); *C12Q 1/18* (2013.01)
(58) Field of Classification Search
  CPC ..... B01L 2325/02; B01L 3/508; C12M 37/06; A61L 2/28
  See application file for complete search history.

(56) References Cited

U.S. PATENT DOCUMENTS

| | | | |
|---|---|---|---|
| 5,856,118 A | | 1/1999 | Dalmasso |
| 5,922,592 A | * | 7/1999 | Tautvydas ................. A61L 2/28 |
| | | | 435/287.7 |
| 2008/0000830 A1 | * | 1/2008 | Mabuchi ............. B01D 67/009 |
| | | | 210/500.23 |
| 2008/0206801 A1 | | 8/2008 | Dallmier et al. |
| 2009/0011457 A1 | * | 1/2009 | Faeh ........................ C12Q 1/18 |
| | | | 435/32 |
| 2013/0288352 A1 | * | 10/2013 | Jehle ........................ C12Q 1/22 |
| | | | 435/287.4 |
| 2015/0160210 A1 | * | 6/2015 | Hanaway ........... G01N 33/6893 |
| | | | 435/6.12 |
| 2017/0058257 A1 | * | 3/2017 | Levner ................... C12M 29/10 |
| 2017/0247742 A1 | * | 8/2017 | Doyle ........................ A61L 2/07 |

FOREIGN PATENT DOCUMENTS

| | | |
|---|---|---|
| WO | WO 96/06184 A1 | 2/1996 |
| WO | WO 2005/098019 A2 | 10/2005 |
| WO | WO 2011/142824 A1 | 11/2011 |
| WO | WO 2012/092684 A1 | 7/2012 |
| WO | WO-2016164329 A1 * | 10/2016 ............... A61B 1/00 |

OTHER PUBLICATIONS

[No Author Listed] Pathogen Safety Data Sheets: Infectious Substances—*Staphylococcus aureus*. Public Health Agency of Canada. 14 pages. https://www.canada.ca/en/public-health/services/laboratory-biosafety-biosecurity/pathogen-safety-data-sheets-risk-assessment/staphylococcus-aureus.html Date provided on International Search Report (for International Application No. PCT/EP2018/076642) is Jan. 1, 2011. Noted on International Search Report as having been retrieved on Oct. 1, 20189.

\* cited by examiner

DEVICE AND METHOD FOR THE MICROBIOLOGICAL EXAMINATION OF WASHING MACHINES

CROSS-REFERENCE TO RELATED APPLICATIONS

This application is a National Stage filing under 35 U.S.C. § 371 of International Application No. PCT/EP2018/076642, filed on Oct. 1, 2018, which claims priority to European Application No. 17193973.9, filed on Sep. 29, 2017, and German Application No. 20 2017 105 965.0 filed Sep. 29, 2017, the entire contents of each of which are incorporated herein by reference.

The invention relates a bioindicator and a method for using the bioindicator for microbiological testing of washing machines. The device according to the invention allows a safe, reliable, cost-effective and easy-to-use microbiological test of the disinfection performance of washing machines. The invention further relates concerns a use of the bioindicator and a kit which preferably contains 10 bioindicators. In particular, the invention relates to a closed bioindicator for a verification of disinfecting processes such as rinsing or washing procedures, in particular in washing machines or dishwashers or any devices by means of which a disinfection process can be carried out or demonstrated. This includes for example, machines with disinfection programs.

BACKGROUND AND STATE OF THE ART

In order to prevent diseases, it is crucial to meet the highest standards of hygiene in sensitive environments such as hospitals. Disinfection devices such as washing machines and dishwashers must be verified regularly for their disinfection performance. Dishwashers must further prove their disinfection performance in sensitive areas.

If a washing machine does not function properly, it can become a breeding ground for pathogens such as a variety of bacteria. These pathogens can be transferred, for example, from an introduced, infected good, such as hospital bed linen, to all items to be washed and disinfected. A washing process with a defective or incorrectly operated washing machine thus offers the microorganisms an ideal opportunity to spread. To prevent the spreading, it is important to ensure that the washing machine is working properly, i.e. that its disinfection performance meets the requirements. The disinfection performance is influenced by many factors. Insufficient disinfection performance can be caused, for example, by operating errors, incorrect programming or incorrect dosing of active ingredients or by a defective disinfection device.

Therefore, health authorities regularly check whether tests of disinfection devices have been carried out. A number of guidelines issued by health authorities, such as the Robert Koch Institute for Infectious Diseases, also require regular testing of such devices.

There are several ways to verify the disinfection performance. For example, the temperature of the disinfector can be recorded directly via a data recorder. With some disinfection procedures, conclusions can be drawn about the success of disinfection. However, this method is mainly suitable for purely thermal disinfection processes. In addition, this method may require expensive retrofitting of data recording equipment.

It is also possible to verify the disinfection performance by means of so-called contact samples. The goods to be disinfected are brought into contact with a culture medium in a plastic dish after the disinfection process. In the laboratory it is subsequently examined whether germ growth has taken place on the culture medium. However, this method is expensive, can only be performed by trained personnel and is prone to errors.

Another type of monitoring is carried out by means of so-called bioindicators. In numerous countries such as Germany or Austria, for example, there are regulations or guidelines for usage of bioindicators. Herein, a germ is introduced into the machine at a certain germ density. After the disinfection run, for example the washing cycle, it is tested whether and to what extent a reduction of germs has taken place.

In particular, disinfection devices which are into contact with so-called risk laundry, in hospitals and old people's homes, must be tested at least every six months.

Well-known are testing methods using bioindicators through so-called open systems, in which the germs of the bioindicator are introduced directly into the washing machine. For example, a small cotton bag with a suitable indicator can be used. These bioindicators have the advantage that no specialized staff are required to carry out the test. As long as the washing machine is working properly, germs are reduced. However, the known methods have several disadvantages. If an appliance does not function properly, all items being washed are contaminated. Thus, the examination process itself represents a health risk. Furthermore, despite the fact that disinfection has not taken place, a dilution of the germ density on the bioindicator may occur, i.e. the test result could still be positive. In the same way, despite successful disinfection, the bioindicator may become contaminated a further time after the test due to improper handling and the test result is negative. In the end, the deficiencies result in repeated tests, additional work and expense. The use of the washing machine for disinfecting and cleaning textiles has to be interrupted for a longer time.

In addition, in some countries there are regulations requiring at least three empty runs of disinfection devices such as dishwashers or washing machines after they have been used for disinfection, if the result of the contamination test does not meet the requirements. This results in a great loss of resources such as drinking water or cleaning agents.

Few closed bioindicators are known from the state of the art, but they have some disadvantages. It was described, for example, that a bioindicator can be used to verify the disinfection of so-called containments, enclosed spaces within laboratories or clean rooms. The bioindicator is to be attached to a wall of a containment to be disinfected with an adhesive tape. However, an adhesive tape is not suitable for fixing the bioindicator to a location inside a washing drum during a washing process. In particular, the laundry could be contaminated by the adhesive.

Furthermore, indicators were proposed to monitor a sterilization process in the form of a semi-permeable bag. After sterilisation, the bag is placed in water, which, in combination with the growth medium it contains, can initiate the growth of residual microorganisms. Therefore, this bag is not suitable for testing washing processes in combination with water, as growth could also be stimulated here. Consistent with this, the use of the indicator in a washing machine or dishwasher or a process to that effect is not disclosed.

Also, an indicator for testing disinfection processes from hydrophilic material is known, but a method for use in washing machines was not described.

Also known is a biological indicator for monitoring disinfection processes using gaseous disinfectants such as hydrogen peroxide. The biological indicator comprises, for example, a metal carrier, which makes it unsuitable for use in liquid-based disinfection processes.

A device for checking a disinfection process with an additional protective layer around a membrane has also been described. This indicator is therefore not simply and efficiently structured and is cost-intensive to produce.

A bioindicator for checking the disinfection performance during washing processes is also known, but it is housed in an impractical and less compact, inflexible and can-shaped container. Therefore, the material costs are very high and a substantial space is taken up by the indicator itself during a washing process. Moreover, the probability of damage to the items to be washed and/or the washing machine itself is significantly increased when using this indicator.

All the above-mentioned indicators furthermore have in common that no sets of indicators are used to monitor washing machines. This leads to a number of disadvantages in the evaluation, such as a higher susceptibility to errors and a lower reliability of test, because, for example, several reference germs cannot efficiently be used simultaneously in a test.

Moreover, a procedure for a testing which is particularly user-friendly and involves sending the indicators to an inspection body has not been described. The aforementioned indicators are in fact not suitable for efficient shipping.

Objective of the Invention

An objective of the invention is to provide a device and a process which does not exhibit the disadvantages of the prior art.

The invention is based in particular on the objective of providing a method as well as a device for efficiently testing the disinfection performance of disinfection devices, in particular washing machines, whereby the method and the device is particularly safe and may be applied with ease and in absence of specialized staff, thereby minimizing or eliminating the risk of incorrect performance. In particular, possible contamination of the entire laundry and any further contamination resulting from the testing as well as the risk of compromised test results should be minimized or prevented.

SUMMARY OF THE INVENTION

According to the invention, the objective is solved by a device according to the independent patent claims. The dependent claims represent preferred embodiments of the invention.

In one aspect, the invention relates to a bioindicator for microbiological testing of washing machines, wherein
the bioindicator comprises a carrier,
the carrier comprises reference germs, wherein
the carrier is enclosed by a semi-permeable membrane.

In the sense of the invention, a bioindicator is preferably understood to be a device which, by comparing the number of microorganisms in a spatially limited area before and after a disinfection process to be tested, allows to evaluate the success of the disinfection process. Spatially limited area in the sense of the invention preferably means an area with an extension between 0.25 cm$^2$ and 100 cm$^2$ and preferably comprises a substantial part of the bioindicator. The disinfection process refers preferably to a process of transforming previously pathogenic microorganisms into a state in which they are no longer pathogenic. Particularly preferred the disinfection process is to kill the microorganisms. The term pathogenic preferably refers to potentially pathogenic. The term disinfection process in the sense of the invention refers particularly preferred to a washing process of a washing machine or a rinsing process of a dishwasher. The disinfection process can be carried out thermally and/or chemically. By measuring the density of microorganisms as reference germs, for example by measuring the density of bacteria before and after a disinfection treatment, the success of the disinfection treatment may be determined. Density or germination density preferably relates to the number per area, particularly preferably the number per cm$^2$. However, it may also be preferred to refer to the number of germs per bioindicator. Success preferably means a reduction of germs by several orders of magnitude, i.e. preferably by a factor of several powers of ten. Typically, a successful germ reduction should result in a reduction of the germ density by preferably at least three orders of magnitude or three log levels, in particular by at least four orders of magnitude or four log levels, very preferably by at least five orders of magnitude or five log levels, in some cases preferably at least six orders of magnitude or six log levels. To prove the germ reduction or to measure the germ density, common methods can be used, such as preferably Gram staining, light microscopic examinations, but also growing a culture on a culture medium.

The term microbiological testing preferably refers to testing for microorganisms, i.e. organisms that are very small and consist of one to a few cells. However, multicellular pathogens such as worms may of course also be meant. In the sense of the invention, microorganisms preferably refer to bacteria, fungi and viruses. Herein, pathogenic microorganisms are of particular interest. In the sense of the invention, bacteria shall include all prokaryotes in which the DNA is freely present in the cytoplasm. In the sense of the invention, bacteria belong preferably to the following strains: Actinobacteria, Firmicutes, Tenericutes, Aquificae, Bacteroidetes, Fibrobacteres, Chlorobi, Chlamydiae, Deinococcus-Thermus, Fusobacteria, Gemmatimonadetes, Nitrospirae, Planctomycetes, Verrucomicrobia Chlamydiae, Proteobacteria, Spirochaetes, Synergistetes, Acidobacteria, Chloroflexi, Chrysiogenetes, Cyanobacterium, Deferribacteres, Dictyoglomi, Thermodesulfobacteria and/or Thermotogae.

Fungal microorganisms refer preferably the following fungi: Yeasts, such as *Malassezia furfur* and *Candida albicans*, dermatophytes, various species of *Aspergillus*, for example *Aspergillus fumigatus* Furthermore, in particular fungi of the genus *Cryptococcus, Rhizopus, Coccidioides* and/or *Histoplasma* shall be included by the term fungal microorganisms.

Viruses are preferentially infectious particles that spread as virions outside cells (extracellular) by transmission, but may multiply as viruses mainly inside a suitable host cell (intracellular). The viruses relevant in microbiological examination in the sense of the invention are preferably viruses of the genera Orthopoxvirus, Parapoxvirus, Molluscipoxvirus, Simplexvirus, Varicellovirus, Cytomegalovirus, Reseolovirus, Lymphocryptovirus, Rhadinovirus, Orthohepadnavirus, Rubiviruses, Flavivirus, Alphacoronavirus, Torovirus, Deltaretrovirus, Lentivirus, Bornavirus, Orthobunyavirus, Phlebovirus, Nairovirus, Hantavirus, Influenza virus A, Influenza virus B, Influenza virus C, Avulavirus, Morbillivirus, Henipavirus, Rubulavirus, Pneumovirus, Metapneumovirus vesiculovirus, mastadenovirus, polyomavirus, dependovirus, erythrovirus, rotavirus, coltivirus, norovirus, sapovirus, hepevirus, enterovirus, hepatovirus and/or rhinovirus.

The term testing preferably relates to checking for the presence of a microorganism and/or parts of a microorganism. It is preferable that checking for the presence of microorganisms can be carried out by determining their number and/or density. Preferably, the number and/or density before and after the disinfection process to be tested and thus the reduction of germs can be determined. It may also be preferable that a known number of microorganisms are present before the disinfection process and that the number of microorganisms can be determined after the disinfection process. The testing can be executed for example by Gram staining, light microscopic examinations, but also by growing a culture on a culture medium.

A washing machine is used for cleaning wash items. In this cleaning process, mechanical forces and water act in combination on the wash items. Detergents are preferably added to the washing water, which, like the temperature of the washing water, are preferably adapted to the material of the wash items as well as the degree and type of soiling. Washing machines are widely used in the clinical sector to clean and preferably disinfect clothing and other textile products.

Carriers are preferably flat elements which are suitable for the uptake of reference germs. A carrier can be of various types, for example it can be rigid or flexible. A wide variety of geometries are possible, for example round, square, especially square, but also other geometric shapes. Flat is preferably to be understood in that the carrier exhibits a larger expansion in two dimensions then a third dimension. For example, the carrier may have an expansion of at least 1 cm in two dimensions, and exhibit a thickness of only a few millimeters (mm) thick or even less than 1 mm.

Various materials are conceivable as carrier material. For example, textile materials made of natural fibres such as cotton are preferred, but polymers are also conceivable as a preferred carrier material.

It is preferred that the carrier is essentially sterile before the reference germs are applied, i.e. that it is free of microorganisms. Free in the sense of the invention means that a microorganism is present on the carrier with a probability of $10^{-1}$, preferably $10^{-2}$, particularly preferably $10^{-3}$, most preferably $10^{-4}$ or less. It may also be preferred that a microorganism is present on the carrier with a probability of $10^{-5}$, $10^{-6}$ or less.

It may also be preferred that the carrier is an inward facing side of the membrane. Inward-facing preferably means the side of the membrane on which the reference germs are located before the test. Thus, the membrane is preferably an outwardly closed shell, the inside of which acts as a carrier and contains reference germs.

Reference germs are preferably microorganisms that can be applied to the carrier in a controlled manner and without health risk for the specialized staff involved. Controlled means that a desired germ density can be achieved during application. It may be preferred to apply a germ density of, for example, preferably at least $10^7$. It may also be preferred to apply a germ density of up to $10^7$. At the same time, the number of germs or germ density should preferably be reduced under the disinfection procedure to be tested in a predictable and error-free verifiable manner. This is preferably understood to mean that a reduction of germs by a factor of at least $10^3$, preferably $10^3$, particularly preferably $10^4$ and most preferably $10^4$ occurs. Thermal or non-thermal disinfection methods can be verified by means of reference germs.

It is preferred that the reference germ shows only a low pathogenic risk in case of possible exposure. Exposure means in particular that a person comes into direct contact with the reference germ and may, for example, ingests the germ(s). In particular, absorption can be oral, inhalative, dermal, intravenous, intramuscular or intraperitoneal. It is preferred that the reference germs react to the disinfection process in a similar way as the microorganisms that typically occur naturally and are to be disinfected, or are identical to them. Preferred reference germs are bacteria, fungi and/or viruses. Preferred examples of bacteria, viruses and/or fungi are *Aspergillus fumigatus, Bacillus subtilis, Bacteroides fragilis, Candida albicans, Candida krusei, Candida tropicalis, Corynebacterium renale, Escherichia coli, Enterobacter casseluiflavus, Enterobacter hormeachei, Enterococcus faecium, Haemophilus 15 influenzae, Klebs pneumoniae, Micrococcus luteus, Enterococcus faecalis, Neisseria gonorrhoeae, Proteus mirabilis, Proteus vulgaris, Pseudomonas aeruginosa, Staphylococcus epidermidis, Staphylococcus aureus, Streptococcus pneumoniae, Streptococcus agalactiae, Mycoplasma hominis, Pseudomonas aeruginosa, Salmonella enterica, Staphylococcus saprophyticus, Streptococcus pyogenes* and/or *Ureaplasma parvum*.

The term membrane refers in particular to a thin layer of a material which influences a material transfer through said layer. Semi-permeability can be achieved mainly by the structure of the membrane, especially by the geometry of recesses or pores within said structure. These can be sufficiently small, for example, that they cannot be traversed by reference germs.

The membrane is preferably between 0.005 and 1 mm thick, particularly preferably between 0.01 and 0.5 mm and especially between 0.05 and 0.1 mm. In combination with the membrane material, the preferred membrane thickness is particularly suitable for achieving desired material properties such as flexibility and stability. In addition, in connection with the preferred pore size, a surprisingly good permeability for water/disinfectant liquid on the one hand and impermeability for the reference germs inside the indicator on the other hand are achieved in a synergistic way. With this preferred design, the objective of the invention may be solved particularly error-free, efficiently, very well reproducibly and safely.

Semipermeable membrane relates preferably to a membrane which is permeable for water and disinfectants dissolved in water, but impermeable for the reference germs.

Preferred membranes include polymer membranes or ceramic membranes. Examples of preferred groups of materials for the production of membranes are zeolites and/or polyamides.

The semipermeable membrane is preferably mechanically, chemically and thermally stable, yet flexible.

It is preferred that the semipermeable membrane of the bioindicator has pores, preferably the size of the pores must be smaller than the diameter of the components to be separated, which are preferably the reference germs. The size of the pores preferably refers to the diameter of the pores. The pores can have, for example or preferably, a size of 0.5 µm.

Different membrane geometries are preferably used depending on the application. It may be preferable to use a flat membrane, i.e. preferably porous films of polymer or ceramic discs, which are coated with a doctor blade or cast, are used for the membrane geometry. In the doctoring or squeegee process, polymer solutions are preferably spread out by means of a metal doctor blade or squeegee and precipitated to a flat membrane by a phase inversion. A phase inversion is a reversal of the phase. The phase primarily refers to the homogeneously present determining physical parameters in a spatial area with a homogeneous chemical composition, such as the physical state. Precipitation is preferably used in chemistry to describe the precipitation of a substance dissolved in a solution. Such membranes are particularly inexpensive, yet effective. It may also be preferred to use capillary-like hollow fibre membranes. A hollow fibre is generally understood to be a fibre which is cylindrical and has one or more continuous cavities in its cross-section. In general, capillary-like tubes or cavities with very small internal diameters are understood to be tubes or cavities with very small internal diameters, which cause physical effects, especially the capillary effect. Physical terms such as "capillary effect" are to be understood in particular as described in the technical literature, for example in "H. Schubert: Capillarity in porous solid systems, Springer Verlag, Berlin". Such membranes are particularly powerful in terms of their filter capacity. It may also be preferable to use so-called wound modules as membranes, i.e. preferably using two flat membrane units that are spirally wound up separated by a fabric. In this way it is possible to filter components of different sizes that need to be separated particularly reliably. It may also be preferable to use multi-channel elements, i.e. preferably, extruded ceramic cylinders or plates, which are flowed through internally coated channels. Extrusion preferably describes processes in which solid to viscous, hardenable materials are forced out of a shaping opening under pressure. Such membranes are particularly reliable. Preferably composite membranes can also be used. With these membranes, an active membrane layer is preferably applied to a porous carrier layer. An active membrane layer can preferably be a membrane layer which, in addition to its geometry, also fulfils a filter function through additional effects, for example through chemical processes. However, it can also be preferably meant that energy has to be added in order to realize the filter function of the membrane. Such membranes can improve the filter characteristics and often exhibit synergistic effects because their filter properties are better than would be expected given the sum of the filter function caused by the geometry and the filter function caused by the additional effects alone.

A carrier which is (at least partially) enclosed by a semipermeable membrane preferably refers to a carrier which is surrounded on all sides by a membrane as if by a shell, so that the reference germs carried by the carrier cannot reach the outside of the membrane. It may also be preferred that the carrier is the inside of the membrane itself, so that the carrier enclosed by the membrane is the surface on the inside of the membrane provided by the membrane, which is surrounded on all sides by the parts of the membrane that do not belong to this surface, as if by a shell. According to the invention, this may also be a cotton sack. It is preferred that the membrane largely adapts to the shape of the carrier material. In this way a particularly compact and space-saving bioindicator can be produced. The reference germs are preferably accessible to the washing/disinfecting liquid like tea in a tea bag and can interact with the liquid (disinfection), but at the same time cannot escape from the inside of the membrane to the outside.

Sealing of the membrane to the outside can preferably be achieved by a welding or bonding process. Welding preferably means a process in which heat is applied until the material melts or heat is applied and preferably additionally pressure is applied to the workpiece.

By means of the preferred embodiment of the bioindicator a particularly simple, robust and inexpensive device may be provided. In this way a particularly simple production of the bioindicator may be achieved, with additional material savings.

The invention solves in a surprising way the objective resulting from the disadvantages of the prior art. The microbiological testing of washing machines by means of bioindicators can be implemented without the need for specialized staff. In contrast to the prior art, a contamination of the entire washing water with pathogenic microorganisms due to a faulty disinfection process cannot occur. Moreover, erroneous test results, which may result from washing off reference germs during the washing process or not rendering the germs harmless, may be impeded. Also, the preferred bioindicators cannot lead to erroneous test results due to germs applied subsequently in the case of incorrect handling. It was surprising that all the disadvantages of known bioindicators could be overcome by the preferred embodiment. Due to the increased safety and reliability in microbiological testing of washing machines as well as the ease in handling the bioindicator, a sustainable and cost-saving testing can be carried out, which does not lead to any interruptions of daily routine washing processes.

In a preferred embodiment of the invention, the bioindicator for microbiological testing of washing machines comprises
a carrier, said carrier having reference germs, and
a semipermeable membrane, wherein
the carrier is enclosed by the semi-permeable membrane, wherein the membrane is a polymer membrane and has pores of a size between 0.1 µm and 2 µm.

It was surprising that a polymer membrane with these pore sizes could be made available, which in addition solves the inventive objective particularly well. It was also surprising that such a polymer membrane in combination with these pore sizes provides a particularly effective filtering of the reference germs on the one hand and a permeability for water or disinfecting liquid on the other hand. While devices of the prior art hardly allowed reproducible results, such that in practice often several devices have to be used in parallel, the preferred device according to the invention allows the material-saving use of less or only one device, equally providing reproducible results. Said preferred embodiment represents a departure from a usual technical approach.

In a preferred embodiment of the invention, the membrane, preferably the polymer membrane, is hydrophobic. Thereby, an immediate soaking of the membrane with the disinfection liquor or the disinfection/washing liquid is possible. The term hydrophobic is used to characterize substances which are essentially not miscible with water and which, for example, allow for a "rolling off" of water at least partially on their surfaces. For example, hydrophobicity may be defined according to the IUPAC (International Union of Pure and Applied Chemistry) definition, which states that hydrophobicity is the combination of non-polar groups or molecules in an aqueous environment. Hydrophobia can also preferably be described by a hydrophobicity scale. For example, a hydrophobic membrane may have an octanol-water partition coefficient greater than 1, in particular significantly greater than 1. The contact angle can also be used as a preferred method of describing hydrophobicity. Preferably, the contact angle refers to the angle that a drop of liquid (water drop) forms with the surface on a surface on said substance. Preferably, a contact angle of approx. 90° means hydrophobicity, likewise an angle of more than 90°. A person skilled in the art knows how to prepare the membrane material so that it is essentially hydrophobic, e.g. by using and/or coating suitable material (e.g. polytetrafluoroethylene, wax and/or paraffin) and a special structuring (lotus plant as an example). A hydrophobic membrane is particularly important as the disinfectant liquor or the disinfectant/washing liquid due to this reaches immediately the introduced bioindicator. In the past, it has always been assumed that a membrane must be hydrophilic to ensure a good flow through with water and/or the disinfecting liquid. The special suitability of a hydrophobic membrane for testing the disinfection performance of a washing machine is therefore a particular surprise. Synergistic effects may occur together with the membrane material used and/or the pore size.

In a preferred embodiment, the polymer membrane is a flexible polymer membrane. A flexible polymer membrane is particularly suitable for use in a washing machine together with laundry to be disinfected. Due to the flexibility, the laundry is not affected and the washing device itself is mechanically less stressed, which increases the durability of the washing device and the laundry. Even with a washroom (washing drum) filled to the brim with laundry, such an indicator can adapt particularly well to the given space conditions.

A flexible polymer membrane is preferably fluid, variable and/or of rubber-type, and essentially dimensionally stable even at high temperatures. The polymer is adaptable and bendable despite being essentially dimensionally stable. It is preferred that flexible polymer is pliable. The person skilled in the art knows that the desired properties may be achieved by choosing preferred thicknesses, material compositions and/or textures. In a preferred embodiment, the polymer membrane is a polymer film.

In a preferred embodiment, the bioindicator is flat. Preferably, the indicator is essentially extended in a plane and only insignificantly along a thickness perpendicular to said plane. Such an indicator makes a particular effective use of the space between the items being washed in a washing machine. In particular, the adaptability to the washing machine and the wash item is synergistically increased.

Terms such as essentially, approximately, about etc. preferably describe a tolerance range of less than ±20%, preferably less than ±10%, particularly preferably less than ±5% and especially less than ±1%. Similar describes preferably entities that are approximately equal. Partly describes preferably at least 5%, particularly preferably at least 10%, and in particular at least 20%, in some cases at least 40%.

Preferably, the indicator exhibits a thickness of less than 1 mm, particularly preferably less than 0.5 mm and especially less than 0.2 mm. Such a carrier is particularly space-saving. Experts have so far assumed that such an indicator is not stable and needs a protective cover. The invention surprisingly overcame this prejudice.

Preferably, the flat indicator has a rectangular shape with edge lengths of less than 4 cm, especially preferably less than 3 cm. Such a compact indicator is particularly suitable for the testing of washing machines, especially filled with items to be washed. It was surprising that such a preferred indicator would allow a particularly safe microbiological test. Safe means that the detection of germs is less error prone than the prior art and furthermore that the items to be washed may not be affected negatively.

In a preferred embodiment of the invention, the carrier is permeable on both sides to a disinfecting liquid. Especially with the surrounding permeable membrane, this results in surprising improvements compared to the prior art. The embodiment enables a particularly effective test to be carried out, as the disinfectant liquid flows through a carrier that is permeable on both sides to a greater extent, thus surprisingly reducing or eliminating the probability of false results.

In a preferred embodiment, the bioindicator is adapted for microbiological testing of washing machines, preferably with items to be washed. This means that the bioindicator exhibits special properties for verifying the washing machines together with items to be washed. In particular, it is flat, has a compact format and is flexible, yet stable. Preferably, the bioindicator is also non-adhesive. If a testing is carried out together with laundry, the testing can be particularly efficient, as the routine washing process does not have to be interrupted.

In a preferred embodiment, the reference germs of the bioindicator are selected from the Firmicutes strain. It is particularly preferred to provide a bioindicator whose reference germs are selected from the enterococci and/or staphylococci family. Enterococci are preferably gram-positive, catalase-negative and aerotolerant, anaerobic bacteria. The spherical (coccoid) bacteria are arranged in pairs or short chains. Enterococci are preferably the following species: *Enterococcus avium, Enterococcus casseliflavus, Enterococcus durans, Enterococcus faecalis, Enterococcus faecium, Enterococcus gallinarum, Enterococcus hirae, Enterococcus raffinosus*. Staphylococci are preferably roundish, grape-like arranged, non-sporeforming gram-positive bacteria without active movement from the group of cocci. Both coagulase-positive staphylococci and coagulase-negative staphylococci may be preferred. Coagulase-positive staphylococci are preferably *Staphylococcus aureus, Staphylococcus agnetis, Staphylococcus delphini, Staphylococcus hyicus, Staphylococcus intermedius, Staphylococcus lutrae, Staphylococcus pseudintermedius* and/or *Staphylococcus schleiferi* subsp. *coagulans*. Coagulase-negative staphylococci are preferably *Staphylococcus epidermidis, Staphylococcus haemolyticus, Staphylococcus lugdunensis* and/or *Staphylococcus saprophyticus* subsp. *saprophyticus*.

It is particularly preferred to use reference germs selected from the species *Enterococcus faecium* and/or *Staphylococcus aureus*. Reference germs of this type are surprisingly suitable for reflecting the reduction of both thermoresistant and non-thermoresistant germs as a result of the disinfection process. These reference germs may be used to carry out microbiological testing of washing machines, by which the disinfection process can also be verified in a surprising way for other germs that occur in routine clinical practice. Likewise, reference germs of the species *Candida Albicans* show preferred characteristics, which makes it an ideal representative of other common germs. Therefore, the significance of testing methods using these germs is particularly high.

Especially the combination of reference germs selected from the species *Enterococcus faecium, Staphylococcus aureus* and/or *Candida Albicans* in combination with a polymer membrane and a pore size between 0.1 µm and 2 µm and a germ density of up to $10^7$ has proven to be a surprisingly advantageous combination.

Reference germs may also preferably be selected from the group *Mycobacterium terrae, Mycobacterium avium, Bacillus atrophaeus, Aspergillus brasiliensis, Trychophyton rubrum, Candida albicans* and/or MS 2 phage. This selection of reference germs enables a microbiological test to be carried out that is individually adapted to the washing machine to be tested and its environment. For example, it may be necessary for a testing of washing machines in tropical countries, where the risk of infection emanates from different viruses and/or bacteria, to use different reference germs than in climatically temperate countries.

It is preferred to apply a germ density of at least $10^6$. Such a bioindicator can be produced particularly easily and costeffectively. It may also be preferred to apply a germ density of up to $10^6$. A bioindicator produced in this way saves work procedures and time. Due to the preferred germ density, a bioindicator can be provided that is individually adapted to the disinfection process to be carried out.

It is particularly preferred to apply a germ density of at least $10^7$. Such a bioindicator is particularly robust against physical influences. It may also be particularly preferred that the reference germs on the carrier have a germ density of up to $10^7$. With the help of such a germ density, a reduction of germs due to disinfection procedures by several orders of magnitude can be detected surprisingly well.

It may also be preferred to apply a germ density of at least $10^8$. This allows a more reliable test to be carried out than is the case with the state of the art. It may also be preferred to apply a germ density of up to $10^8$. This results in a surprising increase in the quality of the testing.

It is particularly preferred to apply a germ density of up to $10^7$. It was surprising that with such a density of germs a particularly reliable test can be executed.

Especially the combination of reference germs selected from the species *Enterococcus faecium, Staphylococcus aureus* and/or *Candida Albicans* in connection with a polymer membrane, a pore size between 0.1 μm and 2 μm and a germ density of up to $10^7$ has proven to be a surprisingly advantageous combination. Due to the high flow rate of the disinfectant liquid through the carrier with the germs in said polymer membrane with said preferred pore size and the simultaneous particularly good filtering of the preferred germs in said membrane, the preferred germ density has proven to be sufficient for an extremely safe and statistically relevant testing. On the one hand it is ensured that a reduction of germs is not triggered by washing out the germs. On the other hand, however, due to the high flow rate with disinfectant of the liquid, a disinfection of the germs can take place with a high degree of certainty, so that a failed killing of the germs is almost certainly not a false alarm, but rather indicates a malfunction of the washing machine.

Typically, a germ reduction of preferably at least three orders of magnitude (factor $10^3$) or log levels should be achieved. Such a reduction of germs can be detected particularly reliably. It is particularly preferred to achieve a germ reduction of at least four orders of magnitude (factor $10^4$) or log levels. The detection methods available for such a reduction save time. It is particularly preferred to achieve a germ reduction of at least five orders of magnitude (factor $10^5$) or log levels. This results in the elimination of errors in the verification. In some cases it is preferred that a germ reduction of at least six orders of magnitude (factor$^{106}$) or log levels is achieved. In this way an improved verification can be provided. With the preferred germ density of up to $10^7$, the above-mentioned germ reduction can be demonstrated without great effort. Surprisingly, common methods such as Gram staining, light microscopic examinations, but also growing a culture on a culture medium can be used to detect the reduction of germs.

Preferably, the germ density is greater than $10^6$, but less than $10^7$, e.g. the germ density can be $5\times10^6$. This represents a technical progress, since a reduction in price, time and material is needed.

It may be preferred to use membrane pores of a size>0.1 μm. These are particularly easy and inexpensive to produce. Pores with a size of <0.1 μm can also be preferred. These result in an improved filter function against some germs. It may also be preferable to use pores not larger than 2 nm. These are suitable for a particularly reliable performance of the test.

In a preferred embodiment, the pores of the membrane have a size<2 μm. These pores have resulted in a surprising increase in the quality of the test procedure. It is particularly preferred that the pores have a size of <1 μm, as this increases the effectiveness of the test procedure. It is particularly preferred that the pores have a size of <0.6 μm. In this way errors in the test procedure can be eliminated.

A preferred pore size is therefore between 0.1 μm and 1 μm, preferably between 0.1 μm and 0.6 μm. Thus, the safety of the testing and a prevention of germs escaping can be further increased, especially in combination with a polymer membrane, reference germs selected from the species *Enterococcus faecium, Staphylococcus aureus* and/or *Candida Albicans* and a germ density of up to $10^7$.

Combinations of aforementioned preferred parameter ranges of pore sizes may also be preferred. Thus, a particularly high degree of flexibility is achieved in adapting the bioindicator to the respective application, whereby technical possibilities are increased.

It was completely surprising that using the preferred pore size a bioindicator could be provided that solved the objective of the invention in a simple and reliable manner. In particular, the preferred pore size facilitate to ensure that none of the preferred reference germs can escape from the inside the membrane to the outside.

In a preferred embodiment the pore size is 2-10 μm, preferably 2-6 μm and especially 2-4 μm. It was surprising that with such large pores the germs can be filtered. At the same time, the flow rate is higher and the performance is increased, while at the same time the price is reduced by lowering material costs.

Preferred membranes can be polymer membranes or ceramic membranes. The membrane materials may preferably include the following materials or material groups: Polysulfone, polyethersulfone, silicones, polyamides, polyamide imide, polyamide urea, polycarbonates, zeolites, polyacrylonitrile, polyethylene, polypropylene, polytetrafluoroethylene, polyvinylidene fluoride, polyvinyl chloride and/or polypiperazinamide. These materials are suitable for a particularly cost-effective production. These materials also surprisingly increase the filter effect. Thereby a synergistic effect may be achieved with regard to the filter function, since the materials themselves, independent of the membrane, improve the filter function.

The membrane may also preferably comprise cellulose, cellulose ester and/or regenerated cellulose. This makes it particularly easy to use recycled materials and save resources as well as costs in the long term.

It may also be preferred that the membrane includes ceramic and/or stainless steel. These materials can be used to provide a membrane with a particularly powerful filter function.

Furthermore, it may be preferred that the membrane comprises silver and/or silicon. These materials can improve the membrane.

Due to the preferred materials for membrane production, a membrane can be provided which both contributes to the solution of the objective of the invention and is also easy to produce. In particular in combination with the preferred pore size, synergistic effects result, which in a surprising way contribute to the fact that no reference germ can reach the outside from the inside of the membrane. It was completely surprising that by combining preferred material and preferred pore sizes, the filter function of the membrane is intact even for reference germs smaller than the pore size.

It is preferred that the carrier exhibits a flat shape. The term flat is preferably to be understood in that that the element has a greater expansion in two dimensions than in a third dimension. The carriers can preferably be essentially round or angular. It may be preferred that the cariers are triangular, square, quadrangular or rectangular, but pentagons or hexagons may also be preferred. It is preferred that the shape is essentially a polygon. By adapting the shape to the application, a particularly advantageous testing method can be carried out.

Due to the preferred flat shape, a bioindicator can be provided, which surprisingly does not disturb the washing process during the microbiological testing of washing machines. Even when the washing machine is full, the loading of the washing machine with the bioindicator does not impair the washing process. Especially in combination with the preferred, flexible embodiment, a synergistic effect results and the adaptability to the load condition of the washing machine can be improved to a greater extent than could be expected by considering the shape and flexibility of the indicator individually. Thus, there is no difference in terms of loading the washing machine with laundry or items to be washed as well as in terms of the quality of the washing process when the washing machine is loaded with the bioindicator compared to a normal washing process without bioindicator.

A washing machine within the meaning of the invention preferably comprises all machines which carry out or can demonstrate a disinfection process. This can also be dishwashers or other machines and devices.

It is preferred that the carrier material includes textile material or textile materials. Natural fibres such as rock wool, cotton fibres, flax fibres, hemp fibres or animal fibres such as wool, silk or fur hairs may be preferred. These materials are characterized by high reliability and low manufacturing costs. Moreover, these carrier materials can surprisingly improve the filter function of the membrane. However, it may also be preferable to use chemical fibres such as viscose, lyocell, rubber or synthetic polymers such as polyacrylonitrile, polypropylene, polyester, polyamide or polyurethane. These are particularly easy to process and save productions steps during the production. Inorganic fibres such as ceramic, glass or metal fibres can also be used. These are characterized by a particular effectiveness as a carrier substance. It may also be preferred that the carrier is identical to the inside of the membrane or at least consists of the same material. This allows to save materials and reduce costs. In this case the carrier material preferably comprises the following materials or groups of materials: Polysulphones, polyethersulphone cellulose, cellulose esters, regenerated cellulose, silicones, polyamides, polyamide imide, polyamide urea, polycarbonates, ceramics, stainless steel, silver, silicon, zeolites, polyacrylonitrile, polyethylene, polypropylene, polytetrafluoroethylene, polyvinylidene fluoride, polyvinyl chloride and/or polypiperazinamide.

The preferred embodiment of the carrier provides for a high degree of flexibility in the production of the bioindicator. Especially the preferred embodiment, wherein the carrier is made of natural fibres such as cotton, results in a particularly simple, robust and inexpensive bioindicator.

It is preferable that the bioindicator comprises a cotton cloth, especially as a carrier on which a contaminated nutrient solution (especially with the reference germs) is applied. Such a bioindicator with such a preferred carrier is particularly easy to produce, yet surprisingly robust.

In a further aspect, the invention thus also concerns a kit containing 2 to 16 bioindicators for the microbiological testing of washing machines. This number of bioindicators improves microbiological monitoring. It is preferred that the kit contains 2 or 4 to 16 bioindicators. It is more preferred that the kit contains 7 to 12 bioindicators. With such a number, the quality of the testing can be increased. It is particularly preferred that the kit contains 8 to 11 bioindicators. Such a number of bioindicators increases effectiveness. A kit containing 10 bioindicators for microbiological testing of washing machines is particularly preferred. With such a kit a particularly reliable verification can be carried out. The kit preferably includes an application sheet, a companion sheet and/or at least one mailing bag. The application form preferably describes instructions for carrying out the test procedure. Accompanying sheet preferably describes a quality assurance form to be filled in by the inspecting person, in which preferably for example the date, data for the assignment of the tested washing machine such as location, the name and signature of the inspector and/or the washing programme carried out are entered. Mailing bag preferably refers to a bag that allows the secure dispatch of the kit by a postal service. By safe it is meant that the kit remains intact and without significant influence on the bacterial density. In the preferred embodiment comprising 4 to 16, preferably 7 to 12, especially preferred 8 to 11, especially 10 bioindicators, it can be tested in a particularly reliable way whether a disinfection process meets the safety standards. If, in exceptional cases, one or even several of the bioindicators do not function properly, for example because the correct germ density of reference bacteria was not applied due an erroneous preparation or because the pores of the membrane were blocked, reliable statements can still be made about the remaining bioindicators. Furthermore, the use of different reference germs, for example 5 bioindicators with the reference germs of the group *Enterococcus faecium* and 5 bioindicators with the reference germs of the group *Staphylococcus aureus*, yields improved statements in relation to the success of the disinfection process for a wider range of germs. The preferred embodiment, which also preferably includes an application form, an accompanying sheet and/or at least one mailing bag, further results in an easier application even for non-specialized users. In particular, professional personnel usual involved in the washing or disinfection process may also use the bioindicators to verify the disinfection performance of the washing machines with which disinfection is to be carried out, e.g. washing machines. Due to the bioindicator in the preferred embodiment and the additional preferred application and/or accompanying sheet, the microbiological test procedure can be conducted straight forward and error-free. The actual verification of the disinfection performance can be carried out by a third party service provider or by the manufacturer of the bioindicator. For this purpose, the bioindicators are simply sent in using the preferably included at least one mailing bag. This simple handling ensures a very reliable test procedure and avoids accidental or deliberate incorrect performance of the test procedure. The simple handling of the test procedure ensures a surprisingly high level of compliance, i.e. preferably a high probability of compliance with the preferred test distances and test sequences. In addition, the bioindicators of such a kit comprising the features described herein may comply with the regulations or guidelines of numerous countries, such as Germany or Austria, with regard to the relevant test procedures relevant. Thus, an improvement of the test procedure can be achieved by using such a kit, as the user can simultaneously carry out his own quality control as well as an inspection as required by a government, if applicable. Costs and working stages can thus be saved. Since the regulations and guidelines are based on the authorities' many years of experience and thus reflect the practice of the inspections relevant here, safety can be increased even further. In addition, the bioindicators described herein represent a new approach to compliance with regulations and/or directives.

A preferred embodiment of the kit comprises 7 to 12 bioindicators, the membrane of which is a polymer membrane with a preferred pore size between 0.1 µm and 2 µm, particularly preferably between 0.1 µm and 1 µm and in particular between 0.1 µm and 0.6 µm, wherein the reference bacteria are selected from the species *Enterococcus faecium*, *Staphylococcus aureus* and/or *Candida Albicans* and the respective bacterial density per indicator is up to $10^7$. Such a kit allows in a surprising manner for improved statistical statements on the disinfection performance of a washing machine, which are not known from prior art and which virtually rule out false statements of the test. The advantages, which are already noticeable for individual bioindicators with the preferred features, thus lead to surprisingly improved statistical statements of the verification, if different germs per indicator are used in one kit. Depending on the size of the pores, either the security against the escape of germs can be improved or the occurrence of a false alarm can be reduced.

In a preferred embodiment, the kit comprises two bioindicators, wherein one bioindicator has reference germs of one species, preferably *Enterococcus faecium*, and the second bioindicator has reference germs of a second species, preferably *Candida Albicans* and/or *Staphylococcus aureus*. Such a bioindicator is particularly easy to produce and handle. The compactness ensures that a wash item may be damaged only in a particular little extent. By using the two reference germs, a comprehensive test of the disinfection performance with regard to several germs can be carried out despite the compactness. It was surprising that especially the combination of *Enterococcus faecium* and *Candida Albicans* or *Staphylococcus aureus* allows a particularly comprehensive, safe and statistically significant testing of washing processes.

In another preferred embodiment, the kit includes 4 bioindicators. Surprisingly, 4 bioindicators have proven to be particularly suitable for a reliable and statistically relevant examination of a disinfection performance.

It may be preferred that the kit also includes at least one cotton bag in which the bioindicators can be placed during the washing process. This can contribute to an additional improvement of the filter function of the membrane and thus increase the safety and reliability of the process. In addition, the washing machine and the laundry can be spared, thus saving costs in the long term.

In a further preferred embodiment, the kit comprises 10 bioindicators, wherein 5 bioindicators have reference germs of one species, preferably *Enterococcus faecium*, in different log levels and 5 bioindicators have reference germs of a second species, preferably *Candida Albicans* and/or *Staphylococcus aureus*, in different log levels. Surprisingly, it was found that this form of the invention results in a particularly high degree of certainty in the examination of the disinfection performance with enormous statistical relevance. The combination of said germs is particularly suitable for a comprehensive statement about the disinfection performance of various, including different types of germs. The preferred combinations of germs have advantageous properties which, with a certain universality, also represent other type of germs commonly occurring. By using different log levels, the statistical significance of the test can be increased enormously. Different log levels preferably denote reference germ counts or densities which differ in the power of ten by at least 1.

A preferred embodiment concerns a kit, wherein the kit contains 2 to 8, preferably 3 to 6, particularly preferably 4 to 6, in particular 5 bioindicators reference germs from the group *Enterococcus faecium* and 2 to 8, preferably 3 to 6, particularly preferably 4 to 6, in particular 5 bioindicators reference germs from the group *Staphylococcus aureus* and wherein the number of bioindicators with reference germs from one group preferably corresponds to the number of bioindicators from the other group.

It is therefore preferred in this embodiment if the kit contains the same number of bioindicators with reference bacteria from the group *Enterococcus faecium* and the same number of bioindicators with reference bacteria from the group *Staphylococcus aureus*. By means of this preferred embodiment the success of disinfection processes may be verified in a particularly reliable way. It is preferred that the kit contains 1 to 8 bioindicators for each reference germ, especially 2 to 8 bioindicators, i.e. a total of 2 to 16 bioindicators, preferably 4 to 16 bioindicators. Such a kit is particularly robust. It is further preferred that the kit contains 3 to 6 bioindicators for each reference organism, i.e. a total of 6 to 12 bioindicators.

In this way an increase in the effectiveness of the kit can be achieved. It is particularly preferred that the kit contains 4 to 6 bioindicators for each reference germ, i.e. a total of 8 to 12 bioindicators. Such a kit helps to eliminate errors during the inspection. In particular, it is preferred that the kit contains 5 bioindicators for each reference germ, i.e. a total of 10 bioindicators. Therefore, it is also possible to use a kit with e.g. 10 bioindicators with the same number of bioindicators with reference bacteria from the group *Enterococcus faecium* and reference bacteria from the group *Staphylococcus aureus*. Surprisingly, it has been found that such a kit leads to a particularly reliable testing of washing machines. In addition, it can be produced at a particularly low cost. The production of such a kit can be particularly well streamlined. In particular, reference germs from the *Enterococcus faecium* and

*Staphylococcus aureus* groups respond to different aspects of a disinfection process. For example, *Enterococcus faecium* has a rather high thermoresistance and can therefore be considered in particular as a representative of thermoresistant germs in the test procedure. Both groups of germs cover the behavior of a large number of germs in their response to a disinfection process. It was completely surprising that the preferred use of five bioindicators each with reference germs from the group *Enterococcus faecium* or *Staphylococcus aureus* made it possible to realize an extremely effective, reliable and economical testing of disinfection processes for washing machines.

The combination of different numbers of indicators and/or reference germs and/or germ densities is particularly flexible due to the processing of the membrane and the bioindicators and is preferably adapted to each customer requirement.

It is advantageous if the kit has a clearly identifiable number on the outer surface, which is preferably applied by a stamp, for example. The kit can be quickly and uniquely identified by said number. Said number may preferably be linked to data such as the disinfection site to be inspected or tested, the reference germs used as well as their density, the date of manufacture of the bioindicator, etc.

The preferred embodiment can surprisingly prevent the kit from being incorrectly assigned. The number can preferably be seen as a redundant identification feature next to the completed accompanying sheet. This prevents a test result resulting from a microbiological test of a washing machine using the kit from being assigned to an incorrect washing machine. Such misclassification could result in high costs and a high health risk of infection due to a non-functioning, incorrectly identified disinfection process.

It is preferred that the individual bioindicators of the kit are presently combined in one flat element. Such a kit contributes to material savings. The shape of the element is essentially preferably rectangular. Surprisingly, such an element is particularly well suited to ensure a smooth wash cycle during the test. The element is preferably visibly divided into the individual bioindicators. This contributes to the safety and reliability of the test procedure, in particular errors in the production of bioindicators can be detected more easily. It is preferred that the element is mechanically stable, yet flexible. Such an element protects the washing machine to be tested as well as the items to be washed and thus helps to reduce costs. Preferably, the assignment number is visible on an edge of the element. This additionally increases safety and reliability, and errors can be better corrected. Both in the preferred embodiment, where the carrier is the inside of the membrane itself, and in the preferred embodiment, where the carrier has textile material or textile materials, it may be preferred that the individual bioindicators are separated from each other by welds of the membrane. In this way, the verification procedure can be improved and there a mutual contamination of the bioindicators can be avoided. It may be preferable to insert double welds between the bioindicators in some places, creating small, non-welded, flat elements between them. These double welds and the small, flat elements can be used to clearly identify the various bioindicators, for example to distinguish the reference germs they carry. This increases reliability, especially in the control of germ reduction. It may also be preferred that the small, flat elements are not carriers of reference germs and can therefore be used to verify the functioning of the bioindicator. In this way errors can be corrected. It may also be preferable for them to carry reference germs in order to check their functionality, but they should not be surrounded by a semi-permeable membrane but an impermeable membrane. In this way the reliability of the procedure can be reviewed and increased. Both functionalities of the small, flat elements can also be preferred at the same time, for example by using different elements differently. This has a synergistic effect on the safety and reliability of the process and the elimination of errors, as these aspects are improved to a degree that goes beyond what can be expected from the individual applications of the small flat elements.

In a further aspect, the invention also concerns a method for microbiological testing of washing machines, comprising preferably the following steps: the removal of at least one bioindicator from a mailing bag, the loading of a washing machine to be tested with the at least one bioindicator, preferably together with an item to be disinfected and/or washed, the completion of the accompanying sheet, the removal and preferably the drying of the at least one bioindicator from the washing machine after the disinfection process, and finally the insertion of the at least one bioindicator and the accompanying sheet into a mailing bag for the purpose of its return and the return of the bioindicator and the accompanying sheet in the mailing bag. The preferred kit is delivered to the testing facility in a mailing bag suitable for secure mailing, preferably by a postal service. The mailing bag can also be used for the safe storage of the kit. Prior to testing, the kit can preferably be removed from the mailing bag. It may be preferable that an accompanying sheet as well as a preferably available second mailing bag for the return shipment also accompany the mailing bag and can be removed. For testing, the machine to be tested, e.g. the dishwasher or washing machine, is loaded with the kit. It may be preferable to add the kit separately or together with the laundry into the washing machine. In the latter case, it may be preferable to add the kit loosely or operatively connected to the laundry. The term "operatively connected" may mean, for example, the connection of the kit to the laundry by means of a cable tie, but also the connection by wrapping the kit in the laundry or by inserting it into a pocket of the laundry. After setting the washing program to be tested, adding the preferred detergent and starting the washing process, the person performing the test can preferably fill in the accompanying sheet. This should preferably include data relevant to the identification of the tested washing machine, the date, name and signature of the person performing the test, the selected washing program and any other relevant information and comments. The completion of the accompanying sheet can of course also carried out at a later point in time before returning the mailing bag. When the washing process is finished, the bioindicator is removed from the washing machine, preferably dried, and then placed in a mailing bag together with the accompanying sheet. This may preferably be a new mailing bag to be included in the delivery, but also the same mailing bag as the one used for the previous delivery. Preferably, the mailing bag already carries the address of the service provider or the testing centre for verification of the reduction of germs. Subsequently the mailing bag and its contents can be shipped. Especially the compactness and preferred flatness of the kit or indicator as well as its safety make the kit or bioindicator suitable for shipping.

It may be preferable that when the washing machine to be tested is loaded with at least one bioindicator, the bioindicator is placed in a cotton bag beforehand in order to increase the safety and reliability of the process and reduce costs.

The at least one bioindicator of this method can advantageously also be present as an element comprising several bioindicators and/or comprising the bioindicators contained in a kit.

By means of this preferred embodiment a surprisingly safe, reliable, efficient, cost-effective and easy-to-use method for microbiological testing of e.g. washing machines can be provided.

It was completely surprising that the preceding method steps ensure an extremely high level of compliance when carrying out the test of the disinfection performance of washing machines. Even non-specialized personnel, some of whom work under high time pressure and for whom testing the disinfection performance may constitute an annoying additional work, are put in a position by the preceding method to carry out a method for the microbiological testing of washing machines error-free and without a great loss of time. In addition, using suitable bioindicators the method may comply with the regulations or guidelines of numerous countries, such as Germany or Austria, regarding the relevant test procedures. In this way, an improvement of the test procedure can be achieved, as the user can simultaneously carry out his own quality control as well as a testing required by a government, if applicable. Costs and work stages can thus be saved. Since the regulations and guidelines are based on the authorities' many years of experience and thus reflect the practice of the inspections relevant here, safety can be increased even further. In addition, the bioindicators presented here represent a new approach to compliance with regulations and/or directives.

In a further aspect, the invention relates to the use of the bioindicator for microbiological testing of washing machines. The person skilled in the art recognizes that the preferred embodiments and advantages of the device and method also apply to their use.

SHORT DESCRIPTION OF THE ILLUSTRATION

DETAILED DESCRIPTION OF THE IMAGE

Figure 1:
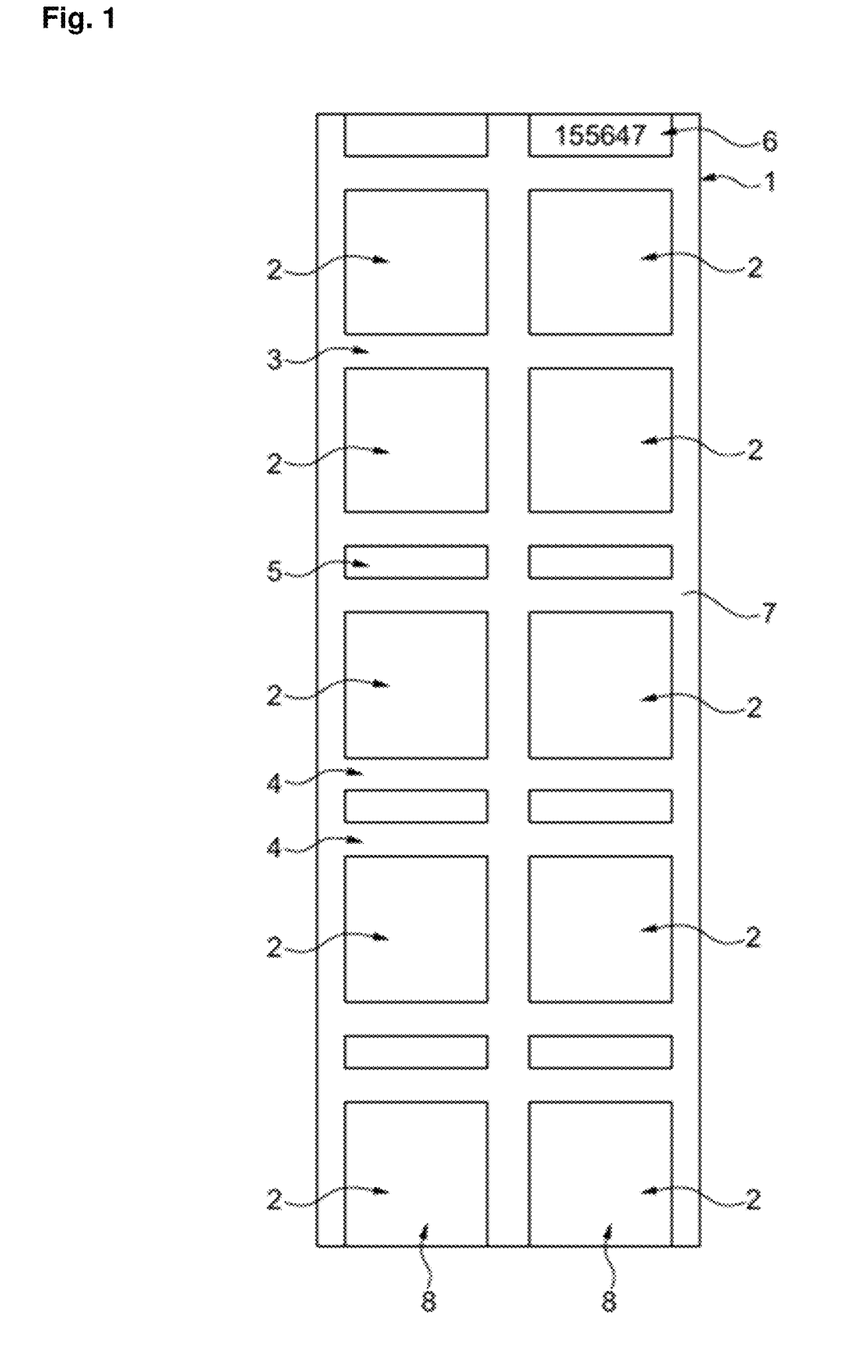
FIG. 1 depicts a schematic top view of a preferred embodiment of the invention comprising a kit containing 10 bioindicators for microbiological testing of washing machines.

FIG. 1 depicts a schematic top view of a preferred embodiment of the invention comprising a kit 1 containing 10 bioindicators 2 for microbiological testing of washing machines. The welds 3 and double welds 4 are present between the bioindicators or the small, flat elements 5 and on the outer edges 7 of kit 1. In the preferred embodiment of the kit shown, the bioindicators 2 are present in pairs next to each other. Five of these pairs 8 are grouped together in a kit. It may be preferable that one bioindicator 2 of pair 8 is provided with a reference organism of the group *Enterococcus faecium* and the other with a reference organism of the group *Staphylococcus aureus*. It may be preferred that in a top view always the left bioindicator of pair 8 is provided with one of the two reference germs and always the right bioindicator with the other. An additional structuring as shown in the preferred embodiment of kit 1 is preferred. For example, it is preferable to place the double welds 4 and the small, flat elements 5 between the lower three pairs 8 (in a top view) of bioindicators 2. Thus, for bioindicator below and above may be easily distinguished as defined in the present drawing. Furthermore, in the preferred embodiment, a uniquely assignable number 6 is well legibly attached to the upper edge, preferably the upper right-hand edge.

Figure 2:
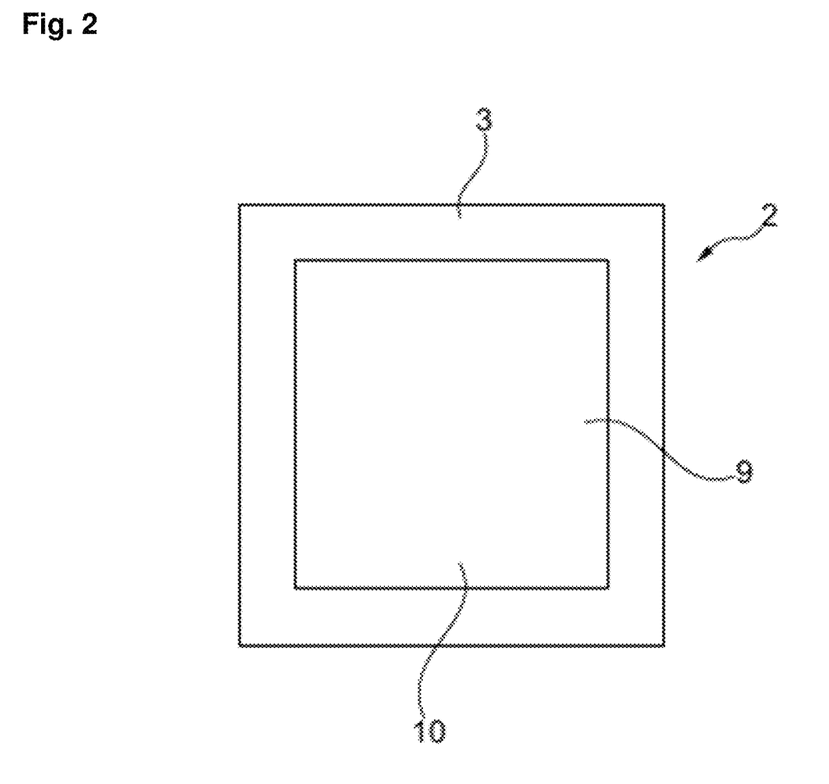
FIG. 2 depicts a top view of a single bioindicator.

FIG. 2 depicts a top view of a single bioindicator 2, with the carrier 9 in the middle and the membrane 10 closed on the outside by a weld seam 3 around the carrier 9.

Figure 3:
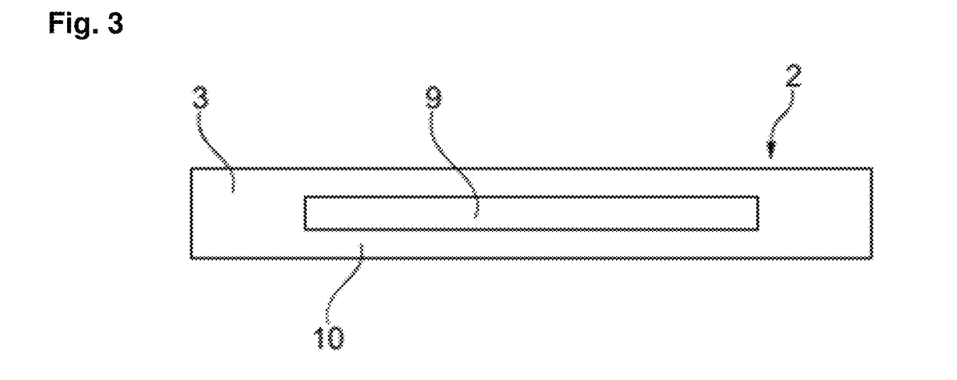
FIG. 3 depicts a cross-section of a single bioindicator.

FIG. 3 depicts a cross-section of a single bioindicator 2, showing that the carrier 9 is enclosed on all sides by the membrane 10. On the sides it is preferably enclosed by a simple weld seam 3.

REFERENCE CHARACTER LIST

1 kit
2 bioindicator
3 single weld seam
4 double weld seam
5 flat elements
6 uniquely assignable number
7 outer edges
8 pairs of bioindicators
9 carrier
10 membrane

The invention claimed is:

1. A kit comprising two to sixteen bioindicators, and comprising an application sheet, an accompanying sheet and/or at least one mailing bag, wherein the individual bioindicators of the kit are presently combined in one flat element, wherein the two to sixteen bioindicators are configured for a microbiological testing of a liquid-based disinfection washing process using water and a disinfectant liquid in a washing machine, wherein each of the two to sixteen bioindicators comprises a flat carrier, the flat carrier has reference germs, the flat carrier is enclosed by a semi-permeable membrane which serves as an outer cover of the two to sixteen bioindicators, the semi-permeable membrane is a polymer membrane and has pores of a size between 0.1 µm and 2 µm, and wherein the semi-permeable membrane is permeable to water and the disinfectant liquid and impermeable to the reference germs and the reference germs are smaller than the pore size of the semi-permeable membrane, the flat carrier has a thickness of less than 1 mm, the semi-permeable membrane has a thickness between 0.005 and 1 mm, the polymer membrane is flexible and mechanically stable allowing the two to sixteen bioindicators combined in one flat element to be used without an additional protective cover for the microbiological testing of the washing process using water and the disinfectant liquid in the washing machine, and the two to sixteen bioindicators combined in one flat element are separated from each other by welds of the semi-permeable membrane.

2. The kit according to claim 1 characterized in that the kit comprises two, four, or ten of the bioindicators.

3. The kit according to claim 1, comprising two bioindicators, wherein a first bioindicator of the two bioindicators comprises reference germs of a first species, and a second bioindicator of the two bioindicators comprises reference germs of a second species.

4. The kit according to claim 1, comprising ten bioindicators, wherein five bioindicators of the ten bioindicators comprise reference germs of a first species in different log levels, and five bioindicators of the ten bioindicators comprise reference germs of a second species in different log levels.

5. The kit according to claim 1, wherein two to eight of the bioindicators comprise reference germs from the group Enterococcus faecium, and two to eight of the bioindicators comprise reference germs from the group Staphylococcus aureus, and wherein the number of bioindicators with reference germs from one group corresponds to the number of bioindicators from the other group.

6. The kit according to claim 3 wherein the first species comprises *Enterococcus faecium*, and the second species comprises *Candida Albicans* and/or *Staphylococcus aureus*.

7. The kit according to claim 4, wherein the first species comprises *Enterococcus faecium*, and the second species comprises *Candida Albicans* and/or *Staphylococcus aureus*.

8. A method for the microbiological testing of a liquid-based disinfection washing process in a washing machine using water and a disinfectant liquid, comprising the following steps:

removing a kit according to claim 1 from a first mailing bag, the kit comprising the two to sixteen bioindicators, and comprising the application sheet, and the accompanying sheet, loading of the washing machine to be tested with the two to sixteen bioindicators together with a good to be disinfected and/or washed, filling in the accompanying sheet, removing and drying the two to sixteen bioindicators, and inserting the two to sixteen bioindicators and the accompanying sheet into a second mailing bag.

9. The kit according to claim 1, characterized in that the semi-permeable membrane is hydrophobic.

10. The kit according to claim 1, characterized in that the two to sixteen bioindicators are flat.

11. The kit according to claim 1, characterized in that the flat carrier is permeable on both sides for a disinfecting liquid.

12. The kit according to claim 1, characterized in that the reference germs are selected from the group Enterococcus faecium and/or Staphylococcus aureus.

13. The kit according to claim 1, characterized in that the reference germs on the flat carrier have a germ density of up to 107.

14. The kit according to claim 1, characterized in that the semi-permeable membrane has pores of a size of <1 µm.

15. The kit according to claim 1, characterized in that the semi-permeable membrane is selected from the group comprising polysulfone, polyethersulfone, silicones, polyamide, polyamide imide, polyamide urea, polycarbonate, zeolites, polyacrylonitrile, polyethylene, polypropylene, polytetrafluoroethylene, polyvinylidene fluoride, polyvinyl chloride and/or polypiperazinamide.

16. The kit according to claim 1, characterized in that the semi-permeable membrane has pores of a size of <0.6 µm.

17. The kit according to claim 1, characterized in that the semi-permeable membrane has pores of a size between of 0.5 µm and 2 µm.

18. The kit according to claim 1, characterized in that the semi-permeable membrane has a thickness between 0.01 and 0.5 mm.

* * * * *